Figure 1:
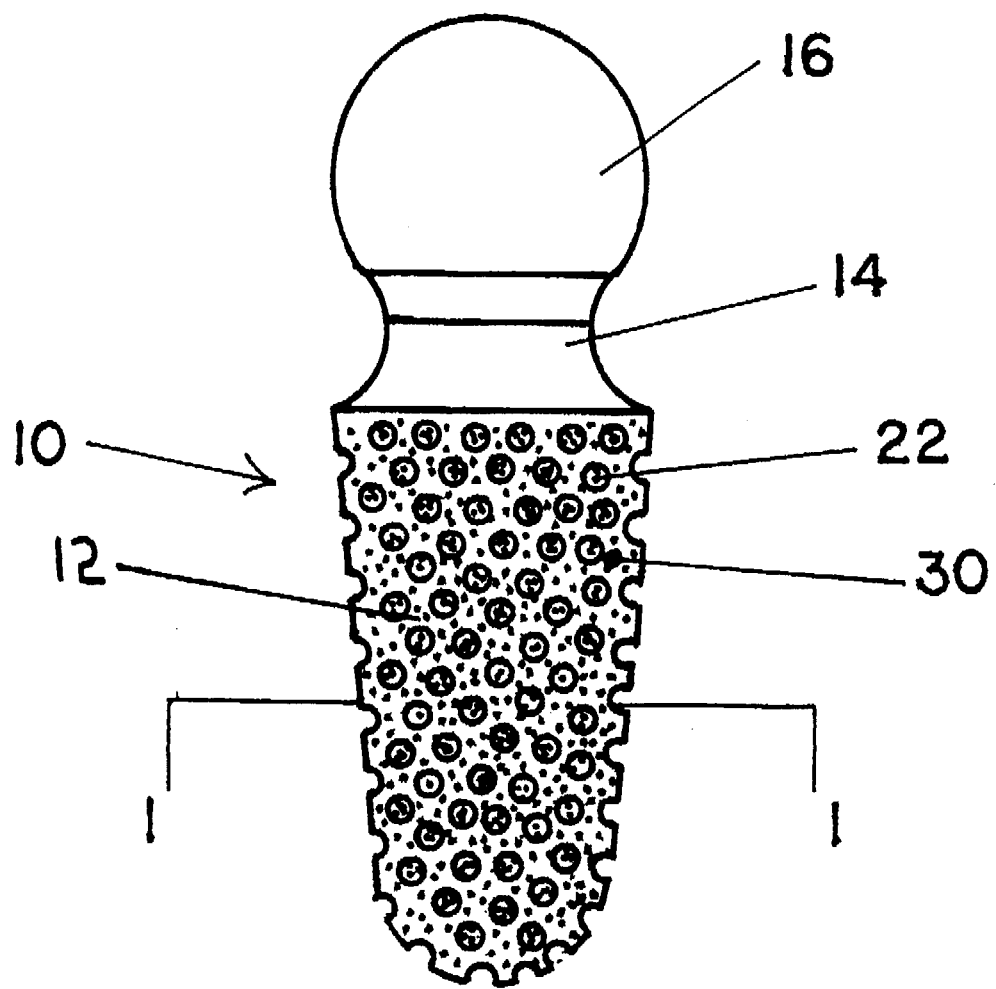
Figure 1A:
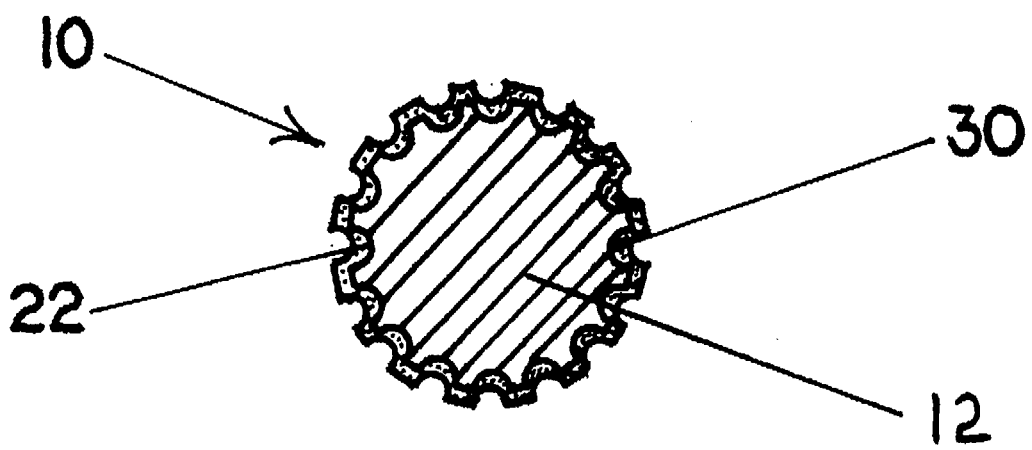

United States Patent [19]

Fontenot

[11] Patent Number: 5,639,237
[45] Date of Patent: Jun. 17, 1997

[54] DENTAL PROSTHESIS HAVING INDENTATIONS

[76] Inventor: Mark G Fontenot, 229 Marilyn Dr., Lafayette, La. 70503-3968

[21] Appl. No.: 488,725

[22] Filed: Jun. 8, 1995

[51] Int. Cl.$^6$ ............................................. A61C 8/00
[52] U.S. Cl. ............................................. 433/173; 433/174
[58] Field of Search ............................................. 433/172, 173, 433/174, 175, 176

[56] References Cited

U.S. PATENT DOCUMENTS

| | | | |
|---|---|---|---|
| 3,855,638 | 12/1974 | Pilliar | 3/1 |
| 3,863,344 | 2/1975 | Pillet | 32/10 A |
| 3,950,850 | 4/1976 | Driskell et al. | 433/176 |
| 4,185,383 | 1/1980 | Heinke et al. | 433/173 |
| 4,468,200 | 8/1984 | Munch | 433/174 |
| 4,474,556 | 10/1984 | Ellis et al. | 433/173 |
| 4,531,916 | 7/1985 | Scantlebury et al. | 433/173 |
| 4,547,157 | 10/1985 | Driskell | 433/173 |
| 4,599,085 | 7/1986 | Riess et al. | 623/16 |
| 4,657,510 | 4/1987 | Gittleman | 433/173 |
| 4,904,187 | 2/1990 | Zingheim | 433/173 |
| 5,002,488 | 3/1991 | Homsy | 433/169 |
| 5,026,280 | 6/1991 | Durr et al. | 433/175 |
| 5,100,323 | 3/1992 | Friedman et al. | 433/173 |
| 5,116,225 | 5/1992 | Riera | 433/174 X |
| 5,123,842 | 6/1992 | Roberts | 433/173 |
| 5,205,746 | 4/1993 | Chanavaz | 433/174 |
| 5,310,343 | 5/1994 | Hasegawa et al. | 433/173 |
| 5,316,476 | 5/1994 | Krauser | 433/173 |

OTHER PUBLICATIONS

*HA–Coated Tooth Replacement: The Integral Implant System*, Academy of Osseointegration, 1991.
*The Future of Implant Dentistry*, Steri–Oss Inc. Product Catalog, 1990.
*Implants, Surgical Kits & Components*, Implant Innovations, Inc., Product Catalog, Rev. 1, Jun. 1991.
*Lifecore Oral Restorative Division*, Lifecore Biomedical, Inc. Product Catalog Sep. 1991.
*The People Who Brough You IMZ, The Leader in Implant Quality and Precision*, Interpore International, May 1991.
*Diagnostic Surgical Restorative and Education Resources*, Implant Support Systems, Inc., 1991.

*Primary Examiner*—Nicholas D. Lucchesi
*Attorney, Agent, or Firm*—Stoel Rives LLP

[57] ABSTRACT

A dental prosthesis, comprising a substantially implant rod constituted of a biocompatible and mechanically suitable material with an anchor end for implanting in a portion of a jawbone and a head end adapted for mounting an artificial tooth or prosthetic device, the rod having a plurality of indentations on at least a portion of the anchor end of the rod, the indentations having concave surfaces with outer perimeters that are substantially circular and at least partially coated with HA, and wherein the anchor end of the rod further contains threaded ridges.

8 Claims, 2 Drawing Sheets

DENTAL PROSTHESIS HAVING INDENTATIONS

BACKGROUND OF THE PRIOR ART

1. Field of the Invention

The present invention relates to an endosseous dental implant having a dimpled surface texture for use in prosthetic reconstruction of the mandible, maxilla, or any craniofacial bones.

2. Description of the Prior Art

The use of cylindrical endosseous dental implants for treatment of various dental, medical, or other conditions is generally well known in the oral and maxillofacial surgery and dental prosthetics field. It has been estimated that in the United States alone, there are in excess of 30 million people that are edentulous in one or both jaws which could benefit from the implantation of 100 million cylindrical endosseous dental prosthetics. Cylindrical endosseous dental implants are commonly used in full arch or partial arch prosthetic reconstruction, secondary reconstruction of craniofacial caner resection, or replacement of single teeth.

The efficacy of a dental implant is primarily dependent upon the surrounding bone's adaptive reformation around and bonding to the implant surface. In particular, the geometry and the quality of such bone reformation determines how much load the bone can resist.

First generation dental implants were typically anchored by mechanical attachment of press-fitted titanium prosthetic implants in the mandible or maxilla. A significant problem of such mechanical fixing resulted from inadequate bone reformation and bonding and consequent failure of the bone when subject to functional loading and resultant shear stresses.

Another cause of dental implants' failure derives from imprecise drilling of the bony site in preparation of the implant. Frequently, the holes are formed by a succession of drillings with several drillbits in incrementally larger diameters selected to correspond with the shape of the implant post. Implant geometry combined with the increased source of operator error introduced by the successive drillings may not result in the desired socket. For example, an oversized socket in which the implant fits loosely may be formed, and is not immediately immobilized resulting in movement when subjected to the stresses of mastication leading to the delayed healing and possible failure of the implant.

Over the past decade, procedures for enhancement of anchoring of dental implants by biochemical bonding of craniofacial bone to an implant surface coated with a substrate have been developed to address the problems of mechanical fixation in the absence of biochemical interfacing. In particular, hydroxylapatite (HA) coatings have been developed which provide for exceptionally strong bonding with bone, in comparison to other biocompatible metal substrates. Typically, HA is plasma sprayed on titanium surfaces.

The biochemical enhancement of bonding occurring at HA-bone interfaces have been observed through histologic and mechanical tests. Histologic tests demonstrate that a HA coating on a titanium alloy provides an osteophilic substrate for enhanced bony proliferation. Such studies indicate that there exists an affinity between bone mineralization and HA, which contrast to the dyschrony between bony proliferation and titanium. The enhanced bonding provided by HA coatings increases the mechanical fixation/anchoring strength of a dental implant two or three times, as compared to metal dental implants of the same geometry.

However, there remain significant problems with HA-coated implants, which largely relate to mechanical limitations of the coating thickness. The mechanical performance of the HA-coated implant is generally inversely related to coating thickness, i.e., a thinner coating of HA has increased mechanical performance. The approximate lower limit for coating thickness is between 10 and 15 microns, the amount of HA surface which may dissolve during the bone implant bonding process. A thickness of about 50 microns is optimal. The upper limit for coating thickness is between 100 and 150 microns, above which susceptibility to shortened service life from fracture or other modes of failure due to shear and tensile fatigue. In view of those limitations on HA coating thickness, the biomedical industry customarily applies coatings ranging between approximately 30 and 90 microns thick.

Unfortunately, notwithstanding the enhanced bonding provided by HA coatings on dental implants, the rate of failure due to shear and tensile fatigue is high as even low loads cannot be withstood along the wall of dental implants with conventional surfaces. Thus, even low functional loads may cause cracking and dislodging of the bone-HA-implant and interfaces.

An additional drawback of HA coatings as applied to prior art surfaces, including threaded or straight-walled implants is cracking, scratching, and stripping of HA often occurs when an implant contacts adjacent surfaces as it is inserted in a jawbone.

Thus, the need for a dental prosthesis with sufficiently strong bonding to the adjacent bony formations of the maxilla and mandible to withstand stress loads, particularly resultant shear and tensile stresses along the shear interface, applied to the dental arches persists.

SUMMARY OF THE INVENTION

Addressing such and other problems of prior art dental implants, the present invention provides a dental endosseous prosthesis, or implant including a substantially cylindrical rod made of a biocompatible and mechanically suitable material with an anchor end for implanting in the maxilla or mandible bone and a head end adapted for mounting an artificial tooth or prosthetic device, the rod having a plurality of indentations on at least a portion of the anchor end of the rod. In a preferred embodiment of the present invention the dental implant has an HA coating fixed to at least a portion of the surface of the anchor end of the rod.

Preferably, the outer perimeters of the indentations on at least a portion of the anchor end of the rod of the present invention are substantially circular, and thereby form a generally dimpled surface. The indentations are shaped and sized so as to maximize the surface area which is encircled within the indentations, and thereby minimize the surface area outside of the indentations. The indentions may be applied to a dental implant having a straight-walled, threaded or other surface.

In a particularly preferred embodiment of the present invention, HA coating on the implant is localized within the perimeter of the indentations of the dental implant. Thus, bone reformation ground and bonding to the implant is limited along the compression component of the concave interface.

The features of the present invention provide multiple advantages. For example, the indented surface increases the surface area and the amount of bond-enhancing biochemical activity in the tooth. Thus, the dental prosthesis of the present invention maximizes the area for bone proliferation and remodelling forming a bond which anchors the prosthesis. The resulting ingrowth into the dimple results in a bone-implant interface which can withstand larger compressive loading. This advantage is further enhanced by restricting the HA coating to the concave surface within the perimeter of the indentations, whereby the biochemical enhancement of HA is constricted to the stronger compression component in the indentation of this implant.

Another advantage provided by the present invention includes the improved mechanical performance imparted by replacing that portion of the smooth walled implant with an indentation. In other words, the weaker shear component of the functioning implant-bone interface is replaced by a convex load bearing implant-bone interface with a greater resistance to failure. In particular, bone-implant interface in the indentation has a large portion of its surface under compression during functional loading.

A still further advantage imparted by the multiple indentations of the present invention is the increased capacity of the prosthesis to conform with the socket drilled to receive the prosthesis and the surrounding bone as it bonds with the prosthesis. This characteristic imparted by the multiple dimples enables the present prosthesis to accommodate, be more conformably implanted, or be forcefully tapped into a hole which may not have a sufficient diameter for a prior art prosthesis of the same outside diameter without the indentations.

An additional feature of the present invention is the use of the HA coating of the present invention as a carrier for medicinal agents. In one embodiment of the present invention, a medicinal agent is coated on the HA coating. The medicinal agent may be a bone morphogenic protein or bone growth hormone, both of which enhance bone formation and bonding around the implanted prosthesis. Alternatively, the medicinal agent coated on the HA can be an antibiotic, which would reduce the risk of infection of the tissue surrounding the incision site.

Figure 2:
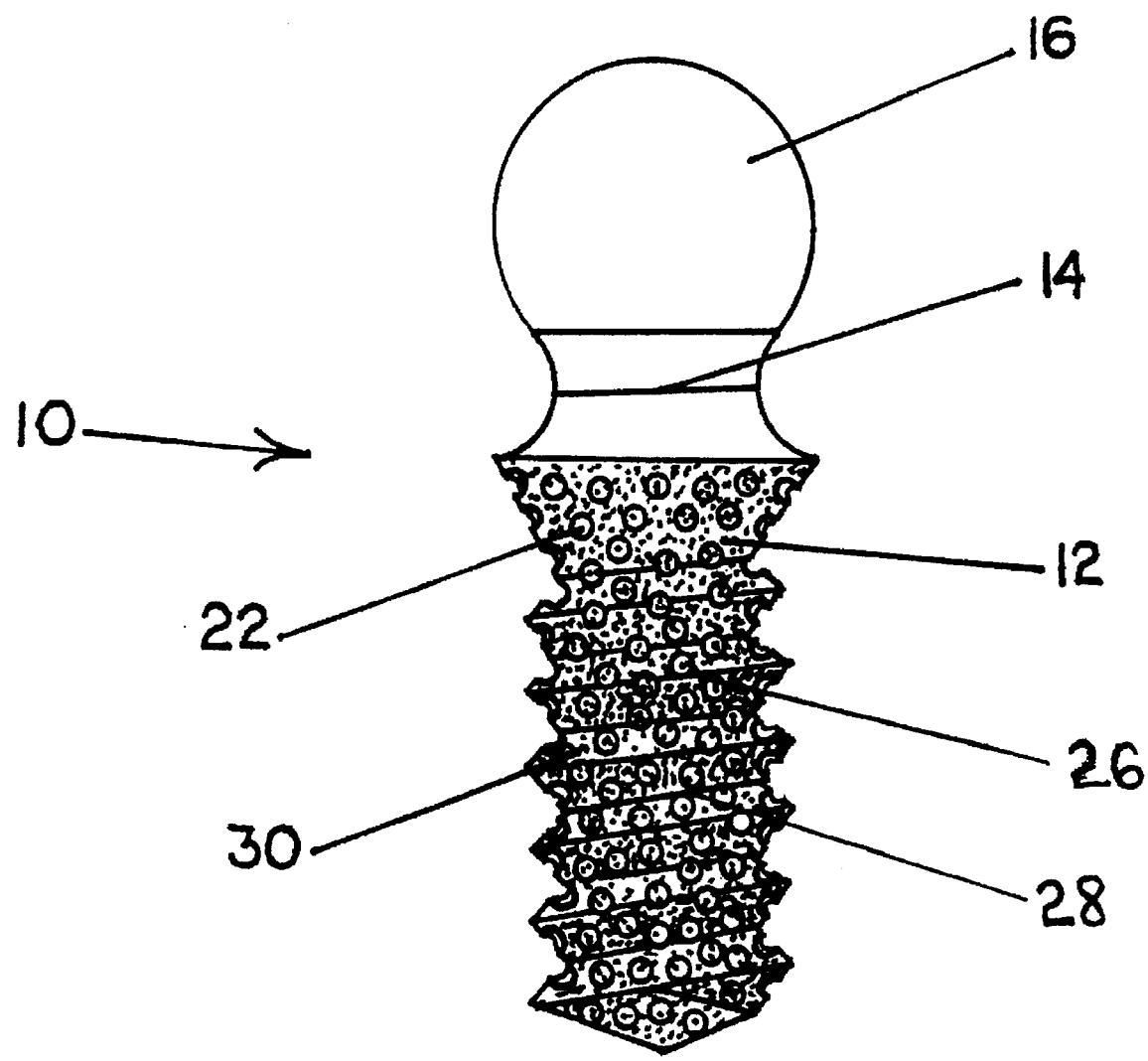

In reference to the drawings in detail, FIGS. 1 to 2 illustrate a preferred embodiment of the present invention. Dental prosthesis 10 has an implant rod 12 integrally attached to a short neck portion 14 to a rounded head 16 and tapering into a implant rod 12. The prosthesis 10 is shown in the upright orientation and will be described as such, with the understanding that the prosthesis is inverted if it is implanted in the maxilla, or lower jawbone. The precise configuration of prosthesis 10 varies according to the location of implantation in the dental arch.

Implant rod 12 is comprised of a metallic material and is preferably a titanium alloy. The head 16 has a configuration adapted for receiving a standard dental appliance (not shown), and is integrally mounted on an anchor end that is in the shape of a truncated cone tapering toward its upper end.

The neck 14 extends through the gingiva when the prosthesis 10 is surgically implanted. As a means for fixation of the implant rod 12 within the alveolar bone through tissue, the implant rod 12 has multiple indentations 22 having circular perimeters which are configured to maximize surface area.

As shown in FIG. 2, in one embodiment of the present prosthesis 10, the anchor end of implant rod 12 has a plurality of annular ridges 26 alternating with a plurality of annular grooves 28 to provide a thread to ease the implantation of the prosthesis 10 in the alveolar bone.

Dental prosthesis 10 further includes an HA coating 30, which is applied by conventional methods known by persons skilled in the art. Such methods employ pressurized spraying of heated HA at a supersonic velocity onto the titanium or other metallic alloy from which the prosthesis core 12 is composed. The thickness of HA coating 30 may range between 15 microns and 75 microns. In the embodiment of the present invention shown in FIG. 2, the indentations 22 are formed by spraying the HA coating 30 according to the aforedescribed method within the perimeter of indentations 22.

The concave dimpled indentations 22 of the healed dental prosthesis 10 according to the present invention result in an interlocking convex bone-concave prosthesis interface that has a greater resistance to displacement. Furthermore, because of the multiplicity of indentations, the overall load bearing capacity until failure of prosthesis 10 is significantly increased.

Furthermore, the prosthesis can be coated with optimal thicknesses of HA which minimize the probability of cracking or fracturing. The thickness of HA coating 30 may range between 15 microns and 75 microns. Thus coating the implant rod with osteophilic HA improves the healing and bone reformation around the prosthesis 10. Bone implant bonding and, therefore, anchoring of the prosthesis 10 is thus maximally secured.

Dental prosthesis 10 is installed utilizing conventional procedures. Such procedures begin by drilling a radial incision in the jawbone to receive dental prosthesis 10. The inner diameter of this hole is equal to or slightly less than the diameter of prothesis 10. As a means of providing immediate immobilization of a dental prosthesis within the alveolar bone, it is common practice to slightly undersize the socket and to force the post or anchor stem in the ostomy hole. Dental prosthesis 10 is then introduced into the hole and forcibly tapped into place with a small mallet. A cover screw to protect the top of the cylinder is typically threaded into the open bore of the cylinder. A slight overfill of the bony site imparts an interference fit of the cylinder in the hole, reducing a movement of the prosthesis during function, which allows bone to heal quickly around the prosthesis. Such bone growth affixes and anchors prosthesis 10 within the jawbone.

What is claimed is:

1. A dental prosthesis, comprising a substantially cylindrical rod constituted of a biocompatible and mechanically suitable material with an anchor end for implanting in a portion of a jawbone and a head end adapted for mounting an artificial tooth or prosthetic device, the rod having a plurality of indentations on at least a portion of the anchor end of the rod, the indentations having concave surfaces with outer perimeters that are substantially circular and at least partially coated with HA, and wherein the anchor end of the rod further contains threaded ridges.

2. The prosthesis of claim 1, wherein HA is coated only on a concave surface within a perimeter of each the plurality of indentations.

3. The prosthesis of claim 1, wherein each indentation is shaped and sized so as to maximize the surface area within the perimeter of each indentation, and thereby minimize the surface area outside each indentation.

4. The prosthesis of claim 1, wherein the HA coating thickness ranges between about 15 microns and about 75 microns.

5. The prosthesis of claim 1, wherein the indentations comprise a carrier containing one or more medicinal agents.

6. The prosthesis of claim 5, wherein the medicinal agent comprises bone morphogenic protein.

7. The prosthesis of claim 5, wherein the medicinal agent comprises bone growth hormone.

8. The prosthesis of claim 5, wherein the medicinal agent comprises an antibiotic.

* * * * *